(12) United States Patent
Wu et al.

(10) Patent No.: US 8,877,283 B2
(45) Date of Patent: Nov. 4, 2014

(54) METHOD FOR PREPARING POROUS HYDROXYAPATITE COATINGS BY SUSPENSION PLASMA SPRAYING

(75) Inventors: Fang Wu, Sichuan (CN); Yi Huang, Sichuan (CN); Lei Song, Sichuan (CN); Xiaoguang Liu, Sichuan (CN); Yanfeng Xiao, Sichuan (CN); Jiamin Feng, Sichuan (CN); Jiyong Chen, Sichuan (CN)

(73) Assignee: Si Chuan University, Chengdu, Sichuan (CN)

( * ) Notice: Subject to any disclaimer, the term of this patent is extended or adjusted under 35 U.S.C. 154(b) by 320 days.

(21) Appl. No.: 13/318,918

(22) PCT Filed: Jul. 9, 2009

(86) PCT No.: PCT/CN2009/072702
§ 371 (c)(1),
(2), (4) Date: Nov. 4, 2011

(87) PCT Pub. No.: WO2010/130109
PCT Pub. Date: Nov. 18, 2010

(65) Prior Publication Data
US 2012/0052183 A1 Mar. 1, 2012

(30) Foreign Application Priority Data
May 12, 2009 (CN) .......................... 2009 1 0302244

(51) Int. Cl.
| A61L 33/00 | (2006.01) |
| A61L 27/32 | (2006.01) |
| C23C 4/12  | (2006.01) |
| C23C 4/10  | (2006.01) |
| A61L 27/56 | (2006.01) |

(52) U.S. Cl.
CPC .................. A61L 27/32 (2013.01); C23C 4/127 (2013.01); C23C 4/105 (2013.01); A61L 27/56 (2013.01)
USPC ............ 427/2.1; 427/189; 427/190; 427/191; 427/195

(58) Field of Classification Search
USPC .......................... 427/2.1, 189, 190, 191, 195
See application file for complete search history.

(56) References Cited

U.S. PATENT DOCUMENTS

| 5,609,921 A    | 3/1997 | Gitzhofer et al. |
| 6,623,796 B1 * | 9/2003 | Van Steenkiste ............. 427/189 |

FOREIGN PATENT DOCUMENTS

CN          1064610 A       9/1992
(Continued)

OTHER PUBLICATIONS

Jaworski et al., Optimization of Dielectric Properties of Suspesion Plasma Sprayed Hydroxyapatite Coatings, 2007, Mat-wiss. u. Werkstofftech, vol. 38 No. 2, pp. 125-130.*

(Continued)

*Primary Examiner* — Dah-Wei D Yuan
*Assistant Examiner* — Andrew Bowman
(74) *Attorney, Agent, or Firm* — Caesar, Rivise, Bernstein, Cohen & Pokotilow, Ltd.

(57) ABSTRACT

The present invention relates to a preparation method for porous hydroxyapatite coatings. In particular, it is a method of using suspension plasma spraying to prepare porous hydroxyapatite coatings, which belongs to the technical field of biomedical material preparations. The present invention added a pore-forming agent into the hydroxyapatite suspension with a solid content of 16%-45%. After full stirring, the feedstock materials for plasma spraying were transferred into the injection system, and injected into the high temperature area of the central plasma flame. Then, the feedstock materials made the heat exchange with the high plasma flame of plasma spraying gun. Then the sprayed raw materials were subjected to breakup and refinement of the droplets, solvent evaporation, the decomposition and gasification of the pore-forming agent and melting of feedstock materials. Finally, the porous hydroxyapatite coatings are directly deposited onto the substrate surfaces of the biomedical materials.

15 Claims, 4 Drawing Sheets

(56) References Cited

FOREIGN PATENT DOCUMENTS

| CN | 101279105 | * | 4/2008 | .............. A61L 27/12 |
| CN | 101250681 A | | 8/2008 | |
| CN | 101250682 A | | 8/2008 | |

OTHER PUBLICATIONS

Jaworski et al., "Optimization of Dielectric Properties of Suspension Plasma Sprayed Hydroxyapatite Coatings", Mat.-wiss. u. Werkstofftech, vol. 38, No. 2, pp. 125-130 (2007).

International Search Report for PCT/CN2009/072702 dated Feb. 11, 2010.

* cited by examiner

METHOD FOR PREPARING POROUS HYDROXYAPATITE COATINGS BY SUSPENSION PLASMA SPRAYING

TECHNICAL FIELD

The present invention is in connection with a preparation method for porous hydroxyapatite coatings, which belongs to the technical field of biomedical material preparations.

TECHNICAL BACKGROUND

Hydroxyapatite (chemical formula: $Ca_{10}(PO_4)_6(OH)_2$) is the main inorganic phase of human body hard tissue, such as bone and teeth, with good bioactivity and biocompatibility. The hydroxyapatite coatings deposited on the biomedical metal substrates by air plasma spraying are ideal hard tissue replacement and repair materials, which combine the excellent mechanical properties of biomedical metal with the good bioactivity and biocompatibility of hydroxyapatite. Hydroxyapatite coatings prepared on the biomedical metal substrates have been used extensively and successfully in commercial applications such as dental implants, artificial joints and other medical implants. The principle of air plasma spraying is as follows: firstly, the hydroxyapatite powders are heated to molten state in a very short time using 5000-10000° C. high temperature plasma flame; then, the molten hydroxyapatite is propelled to the surface of biomedical metal at a high speed of 300 m/s, to form strong adhesion between the hydroxyapatite coating and the biomedical metal. However, the hydroxyapatite coating deposited on the implant surface is usually dense and the porosity is small, and a scanning electron microscopy (SEM) micrograph is shown in FIG. 1. After the implants are put into the defect site, it is difficult to grow the new tissue into the implant surface, thus affecting the early fixation and long-term stability of the implants.

The preparation of porous hydroxyapatite coatings is the best way to solve the above problem caused by the dense implant surface. However, due to the restriction of the specific principle of the plasma spraying, it is very difficult to prepare the porous hydroxyapatite coatings using air plasma spraying and to get the hydroxyapatite coatings with the good porous structure. The porous titanium coatings have been deposited on the implant surfaces by air plasma spraying. The porous titanium coatings not only have a good three-dimensional porous structure, but also possess good mechanical properties. However, owing to its bio-inertness, it is usually in need of subsequent biological activation to improve the bioactivity, such as acid treatment, alkali treatment, acid-alkali treatment, and anodic oxidation. Usually, these treatments often need very long process times, and the bioactivity of the porous titanium coatings treated by alkali treatment is less than that of the porous calcium phosphate materials, thus needing a longer time to form new bone. (Takemoto M, Fujibayashi S, Neo M, Suzuki J, Matsushita T, Kokubo T, Nakamura T. Osteoinductive porous titanium implants: Effect of sodium removal by dilute HCl treatment. Biomaterials, 2006, 27(13): 2682-2691.)

The previous studies of the inventors (CN101250681 and CN101250682) provide a method and equipment for preparing bioactive hydroxyapatite coatings through the suspension plasma spraying process. The method selects the liquid precursor plasma spraying process, instead of the air plasma spraying process. In the process, the hydroxyapatite suspension is transferred into the suspension injection system by peristaltic pump. Then, the hydroxyapatite suspension is injected into the high temperature area of the plasma flame, where the suspension makes the heat exchange with the high temperature plasma flame from the plasma spraying gun. Then the suspension is subjected to breakup and refinement of the droplets, solvent evaporation, and melting of spraying raw materials. Finally the bioactive hydroxyapatite coatings with a uniform structure are directly deposited on the substrate surfaces of the biomedical metal materials. Moreover, in the suspension plasma spraying preparation for making porous hydroxyapatite coatings, it directly selects the spraying feedstock materials prepared through wet chemical method, which avoids the complicated preparation processes for APS feedstock materials, such as aging after wet chemical synthesis, spraying drying, powder granulation and spheroidization, calcination, ball milling and sieving. It shortens the total process time and cuts the process costs.

SUMMARY OF THE INVENTION

The technical problem that the present invention aims to solve is to provide a method for preparing porous hydroxyapatite coatings. The method is a further improvement based on the previous research achievements of the inventors, which prepare bioactive hydroxyapatite coatings using suspension plasma spraying process. The current invention prepares the bioactive hydroxyapatite coatings with porous structure, which would greatly improve the biological properties of the coatings, such as bioactivity and capability for bone ingrowth.

The technical solution of the invention is as follows: the pore-forming agent is added into the hydroxyapatite suspension; through the decomposition and gasification of the pore-forming agents, the fragmentation and refining of the hydroxyapatite suspension droplets, solvent evaporation, and melting of feedstock materials, hydroxyapatite coatings with porous structure are deposited on the substrate surfaces of the biomedical materials.

For the purpose of the present invention, the solid content of the hydroxyapatite suspension is 16%-45%. The aforementioned pore-forming agents are ethanol, ammonium carbonate, ammonium bicarbonate, hydrogen peroxide and deionized water.

When the ammonium carbonate or ammonium bicarbonate is selected as the pore-forming agent, the addition of the ammonium carbonate or ammonium bicarbonate is 5%-65% (preferred 10%-40%) with the solid content of the suspension being referred to as 100%.

When the ethanol or hydrogen peroxide is selected as the pore-forming agent, the addition of the ethanol or hydrogen peroxide is 10%-80% (preferred 20%-50%) with the solid content of the suspension being referred to as 100%.

When the deionized water is selected as the pore-forming agent, a specific amount of the deionized water is added to the suspension with a final solid content of 5%-15%. During the spraying process, the gasification of the deionized water can also help to obtain the porous structure of the coatings.

The above-mentioned hydroxyapatite suspension can be prepared using the existing technology. For example, diammonium phosphate solution is added into the calcium nitrate solution. Then the ammonia is added into the above solutions, in order to control the pH value of the solution to 9-12 for reaction. Followed by standing and aging, the hydroxyapatite suspension is obtained.

The invention may select a small-angle atomization nozzle or a small-diameter catheter, which directly inject the plasma spraying feedstock materials into the high temperature area of the central plasma flame through the radial direction.

Specifically, the implementation of the invention includes the following steps:

a. Preparation of the Hydroxyapatite Suspension

The 1.2-3.6 mol/L diammonium phosphate solution is added into a stirred 1-3 mol/L calcium nitrate solution according to the Ca/P molar ratio of $Ca_{10}(PO_4)_6(OH)_2$. The pH value of the solution mixture was adjusted to 9-12 with 30 wt% ammonia solution and the reaction was kept at 30-90° C. for 5-15 min, followed by the aging for 24-48 h. After the above steps, the hydroxyapatite suspension with a solid content of 16%-45% is obtained.

b. Addition of the Pore-Forming Agent

The ammonium carbonate, ammonium bicarbonate, ethanol, hydrogen peroxide or deionized water is added into the above suspension, and the mixture is extensively stirred to be used as the feedstock materials for plasma spraying. If the solid content of suspension is referred to as 100%, the addition of the ammonium carbonate or ammonium bicarbonate is 5%-65% (preferred 10%-40%). If the volume of suspension is referred to as 100%, the addition of ethanol or hydrogen peroxide is 10%-80% (preferred 20%-50%). When the deionized water is selected as the pore-forming agent, the amount of the deionized water is added until the suspension solid content is 5%-15%.

c. Transferring the Spraying Liquid into the Injection System

The technician can select either the electronic peristaltic pump or the pressure from the compressed air to transfer the spraying liquid into the injection system. The transferring tube is pressure tube and the diameter is 5-10 mm.

The pressure of the compressed air is 0.15-0.6 MPa (preferred 0.2-0.5 MPa). The transferring rate of electronic peristaltic pump is 10-100 ml/min (preferred 15-90 ml/min).

d. Injection and Plasma Spraying of the Liquid Feedstock Materials

The liquid feedstock is atomized by small-angle atomization nozzle or the liquid feedstock is injected through a small-diameter catheter in the form of linear jet flow. The liquid feedstock is injected into the high temperature area of the central plasma flame, where the suspension makes the heat exchange with the high temperature plasma flame of plasma spraying gun. Then the suspension is subjected to fragmentation and refining of droplets, solvent evaporation, decomposition and gasification of the pore-forming agent, and melting of the feedstock materials, finally the porous hydroxyapatite coatings are directly deposited on the substrate surfaces of the biomedical metal materials.

The droplet spray angle of the above small-angle atomization nozzle is 10-25 degree. Using the smaller spray angle ensures the suspension being injected into the high temperature area of the plasma flame as much as possible, which improves the efficiency of coating deposition and reduces the production costs.

The inner diameter of the small-diameter catheter is 60-280 microns. Using the small-diameter catheter ensures the suspension being injected into the high temperature area of the plasma flame as much as possible, which improves the efficiency of coating deposition and reduces the production costs.

The above-mentioned biomedical substrate materials are biomedical titanium, or biomedical titanium alloy, or biomedical stainless steel, or biomedical cobalt-based alloys, or other biomedical metal materials, or biomedical composite containing metal, or biomedical ceramic materials, or biomedical composite containing ceramics.

Compared with the existing technology, the current invention has the following technical advantages:

1. With regard to the preparation of feedstock materials for plasma spraying, the invention avoids a series of complicated processes involved in the powder feedstock preparation of air plasma spraying. Therefore, the invention not only improves the production efficiency, but also reduces the production costs.

2. The present invention selects deionized water and ethanol as the pore-forming agent, which is easy to volatilize at the high temperature condition. Or, the present invention selects hydrogen peroxide, ammonium carbonate or ammonium bicarbonate as the pore-form agent, which is easy to decompose or gasify. These pore-forming agents do not generate residual impurities in the porous hydroxyapatite coatings, which do not affect the biocompatibility of the porous hydroxyapatite coatings.

3. The porous hydroxyapatite coatings are beneficial to the delivery of oxygen and nutrients and the excretion of metabolites. The porosity of the porous hydroxyapatite prepared by this invention is 2%-50%, and the pore size is 0.1-200 microns. Its bioactivity is better than the coatings prepared without the pore-forming agent, which can promote the proliferation and growth of the osteoblast cells.

DETAILED DESCRIPTION OF PREFERRED EMBODIMENTS

Figure 1:
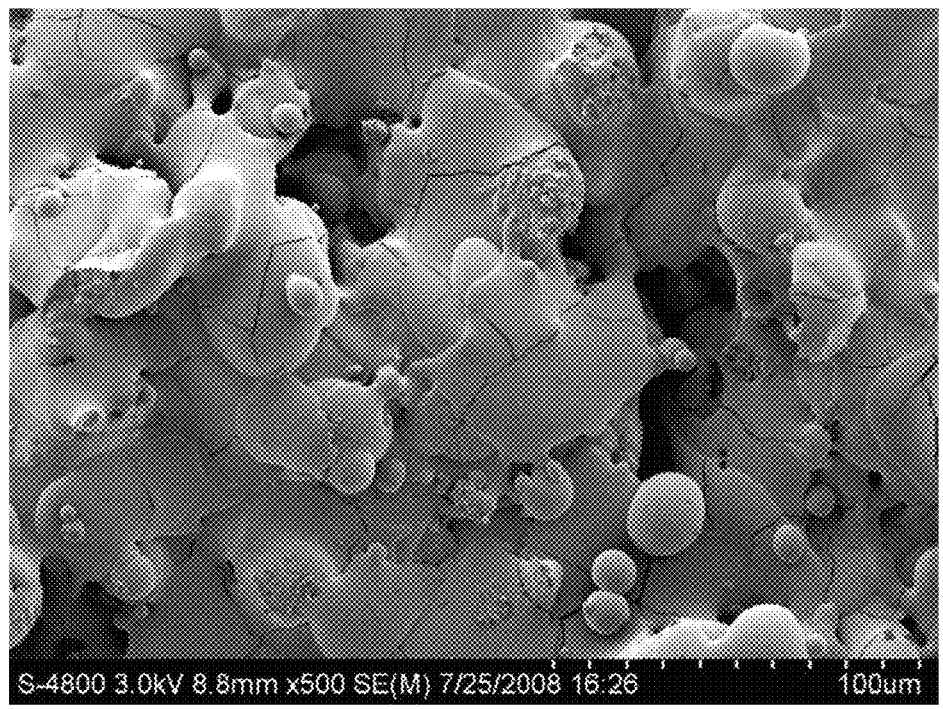
FIG. 1: SEM micrograph of hydroxyapatite coating prepared by the air plasma spraying process.

The technical solution of the invention is as follows: the pore-forming agent is added into the hydroxyapatite suspension with a 16%-45% solid content, which is injected into the high temperature area of the plasma flame; then the decomposition and gasification of the pore-forming agent take place, which ensures the formation of the porous structure of hydroxyapatite coatings during the following processes, including the fragmentation and refining of hydroxyapatite suspension droplet, solvent evaporation, melting of feedstock materials and coating deposition on the substrate surfaces of biomedical materials.

The above-mentioned hydroxyapatite suspension's solid content is 16%-45%. The pore-forming agents include ethanol, ammonium carbonate, ammonium bicarbonate, hydrogen peroxide or deionized water.

The above-mentioned biomedical substrate materials can be commonly-used materials in the field of biomedical materials. However, these materials should be able to withstand the high temperature from the plasma spraying, e.g., biomedical metal materials and biomedical ceramic materials. The biomedical metal substrate materials are biomedical titanium, or biomedical titanium alloy, or biomedical stainless steel, or biomedical cobalt-based alloys, or other biomedical metal materials, or biomedical composite containing metal, or biomedical ceramic materials, or biomedical composite containing metal. The biomedical ceramic materials are alumina ceramic, or zirconia ceramic, or other biomedical ceramic materials, or biomedical composite containing ceramic.

When ammonium carbonate or ammonium bicarbonate is selected as the pore-forming agent, the addition of the ammonium carbonate or ammonium bicarbonate is 5%-65% (preferred 10%-40%), with the solid content of suspension being referred to as 100%.

When ethanol or hydrogen peroxide is selected as the pore-forming agent, the addition of ethanol or hydrogen peroxide is 10%-80% (preferred 20%-50%) with the solid content of suspension being referred to as 100%.

When deionized water is selected as the pore-forming agent, a specific amount of the deionized water is added to the suspension with a final solid content of 5%-15%. During the spraying deposition process, the gasification of the deionized water also can also help to obtain the porous structure of the coatings.

The above-mentioned hydroxyapatite suspension can be prepared using the existing technology. For example, diammonium phosphate solution is added into the calcium nitrate solution. Then the ammonia is added into the above solutions, in order to control the pH value of the solution to 9-12 for reaction. Followed by standing and ageing, the hydroxyapatite suspension is obtained.

The invention may select a small-angle atomization nozzle or a small-diameter catheter, which directly inject the plasma spraying feedstock materials into the high temperature area of the central plasma flame through the radial direction.

One implementation of the invention includes the following steps:

a. Preparation of the Hydroxyapatite Suspension

The 1.2-3.6 mol/L diammonium phosphate solution is added into a stirred 1-3 mol/L calcium nitrate solution according to a Ca/P molar ratio of $Ca_{10}(PO_4)_6(OH)_2$. The pH value of the solution mixture was adjusted to 9-12 with 30 wt % ammonia solution and the reaction was kept at 30-90° C. for 5-15 min, followed by aging for 24-48 h. After the above steps, the hydroxyapatite suspension with a solid content of 16%-45% is obtained.

b. Addition of the Pore-Forming Agent

Ammonium carbonate, ammonium bicarbonate, ethanol, hydrogen peroxide or deionized water is added into the above suspension, and the mixture is extensively stirred to be used as the feedstock materials for plasma spraying. If the solid content of suspension is referred to as 100%, the addition of the ammonium carbonate or ammonium bicarbonate is 5%-65% (preferred 10%-40%). If the volume of suspension is referred to as 100%, the addition of ethanol or hydrogen peroxide is 10%-80% (preferred 20%-50%). When deionized water is selected as the pore-forming agent, the amount of the deionized water is added to the suspension solid content of 5%-15%.

c. Transferring the Spraying Liquid into the Injection System

The technician in the field can select the electronic peristaltic pump or the pressure from the compressed air to transfer the spraying liquid into the injection system. The transferring tube is pressure tube and the diameter is 5-10 mm.

The pressure of the compressed air is 0.15-0.6 MPa (preferred 0.2-0.5 MPa). The transferring rate of electronic peristaltic pump is 10-100 ml/min (preferred 15-90 ml/min).

d. Injection and Plasma Spraying of the Liquid Feedstock Materials

The liquid feedstock is atomized by small-angle atomization nozzle or the liquid feedstock is injected through a small-diameter catheter in the form of linear jet flow. The liquid feedstock is injected into the high temperature area of the central plasma flame, where the suspension makes the heat exchange with the high temperature plasma flame of plasma spraying gun. Then the suspension is subjected to fragmentation and refining of droplets, solvent evaporation, decomposition and gasification of the pore-forming agent, and melting of the feedstock materials, finally the porous hydroxyapatite coatings are directly deposited on the substrate surfaces of the biomedical metal materials.

The droplet spray angle of the above small-angle atomization nozzle is 10-25 degrees. Using the smaller spray angle ensures the suspension being injected into the high temperature area of the plasma flame as much as possible, which improves the efficiency of coating deposition and reduces the production costs.

The inner diameter of the small-diameter catheter is 60-280 microns. Using the small-diameter catheter ensures the suspension being injected into the high temperature area of the plasma flame as much as possible, which improves the efficiency of coating deposition and reduces the production costs.

The above-mentioned plasma spraying power is 20-70 kW. The distance between the biomedical substrate and the plasma spraying nozzle is 8-18 cm. If the plasma spraying power is too low, it is difficult to obtain the coatings; if the plasma spraying power is too high, it is difficult to get the coatings with porous structure. The suitable spraying distance is the key factor to determine the porous structure of the coatings.

The following specific examples further describe the details of the invention. However, they should not be understood as limiting the invention. All amendments, replacements and changes based on the idea of the present invention belong to the present invention.

EXAMPLE 1

The Preparation of the Porous Hydroxyapatite Coating from the Present Invention

Figure 3:
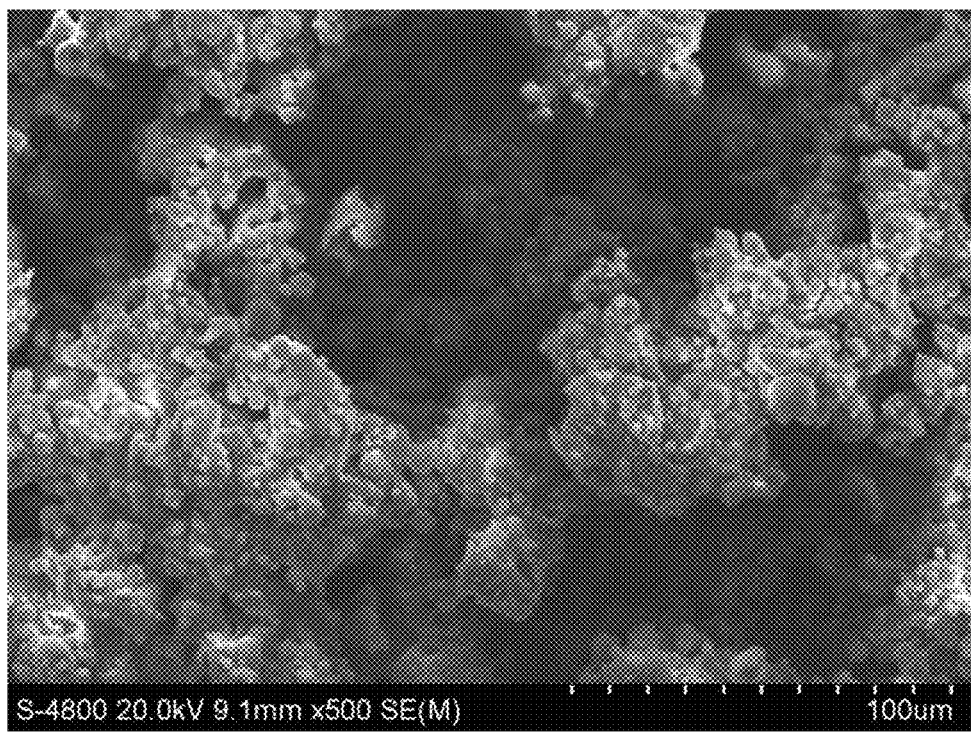
FIG. 3: SEM micrograph of hydroxyapatite coating prepared by the suspension plasma spraying process (with the addition of ethanol as the pore-forming agent).

The 2.4 mol/L diammonium phosphate solution is added into a stirred 2 mol/L calcium nitrate solution on the basis of a Ca/P molar ratio of $Ca_{10}(PO_4)_6(OH)_2$. The pH value of the solution mixture is adjusted to 10 with 30 wt % ammonia solution and the reaction was kept at 70° C. for 20 min, followed by aging for 24 h. After the above steps, hydroxyapatite suspension with a 30% solid content is obtained. The pore-forming agent ethanol is added into the hydroxyapatite suspension. If the volume of suspension is referred to as 100%, the volume of the added ethanol is 30%. The compressed air with 0.2 MPa pressure is used as the transferring power. The pressure tube with a diameter of 5 mm is used as the transferring tube. The hydroxyapatite suspension with the addition of the pore-forming agent ethanol is transferred into the small-angle atomization nozzle with the spray angle of 15 degree. The atomization nozzle uses the compressed air as the atomization gas and the atomization pressure is 0.15 MPa. After the atomization, the hydroxyapatite suspension is directly injected into the high temperature area of the plasma flame through radial direction. The plasma flame is generated by the direct current plasma spraying device. The spraying power is 40 KW and the spraying distance is 12 cm. The hydroxyapatite suspension makes the heat exchange with the high temperature plasma flame. After the suspension is subjected to fragmentation and refining of droplets, solvent evaporation, decomposition and gasification of pore-forming agent, and melting of spraying feedstock materials, the porous hydroxyapatite coatings are directly deposited on the biomedical titanium substrate surfaces. The SEM micrograph of the coating is shown in FIG. 3.

EXAMPLE 2

The Preparation of the Porous Hydroxyapatite Coating from the Present Invention

Figure 4:
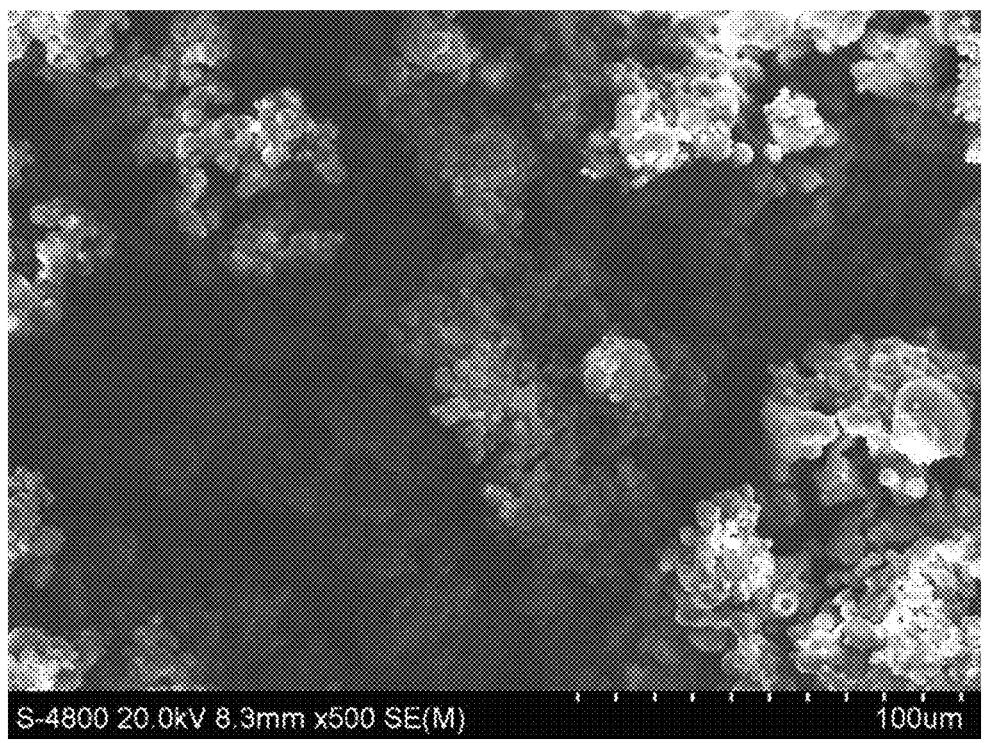
FIG. 4: SEM micrograph of hydroxyapatite coating prepared by the suspension plasma spraying process (with the addition of deionized water as the pore-forming agent).

The 1.5 mol/L diammonium phosphate solution is added into a stirred 1.3 mol/L calcium nitrate solution on the basis of a Ca/P molar ratio of $Ca_{10}(PO_4)_6(OH)_2$. The pH value of the solution mixture is adjusted to 11 with 20 wt % ammonia solution and the reaction was kept at 60° C. for 15 min, followed by aging for 48 h. After the above steps, hydroxyapatite suspension with a 20% solid content is obtained. The pore-forming agent deionized water is added to make the final suspension solid content of 10%. The compressed air with 0.5 MPa pressure is used as the transferring power. The pressure tube with a diameter of 10 mm is used as the transferring tube. The hydroxyapatite suspension with the addition of the pore-forming agent deionized water is transferred into the small-diameter catheter with an inner diameter of 200 microns. The spraying liquid is injected into the high temperature area of the central plasma flame through the small-diameter catheter in the form of linear jet flow. The plasma flame is generated by the direct current plasma spraying device. The spraying power is 60 KW and the spraying distance is 18 cm. The hydroxyapatite suspension makes the heat exchange with the high temperature plasma flame. After the suspension is subjected to fragmentation and refining of droplets, solvent evaporation, decomposition and gasification of pore-forming agent, and melting of spraying feedstock materials, the porous hydroxyapatite coatings are directly deposited on the biomedical titanium alloy substrate surfaces. The SEM micrograph of the coating is shown in FIG. 4.

EXAMPLE 3

The Preparation of the Porous Hydroxyapatite Coating from the Present Invention

Figure 5:
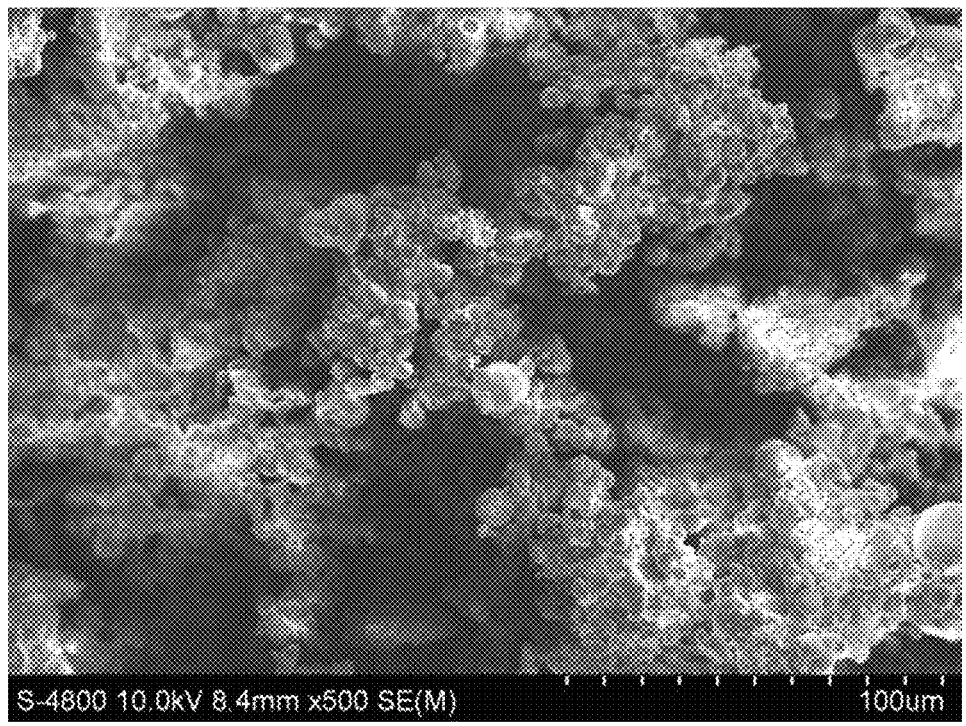
FIG. 5: SEM micrograph of hydroxyapatite coating prepared by the suspension plasma spraying process (with the addition of ammonium carbonate as the pore-forming agent).

The 2 mol/L diammonium phosphate solution is added into a stirred 1.7 mol/L calcium nitrate solution on the basis of a Ca/P molar ratio of $Ca_{10}(PO_4)_6(OH)_2$. The pH value of the solution mixture is adjusted to 9 with 30 wt % ammonia solution and the reaction was kept at 80° C. for 10 min, followed by aging for 24 h. After the above steps, hydroxyapatite suspension with a 25% solid content is obtained. The pore-forming agent ammonium carbonate is added into the hydroxyapatite suspension. If the solid content of suspension is referred to as 100%, the amount of the added ammonium carbonate is 10%. The electronic peristaltic pump is used as the transferring power. The pressure tube with a diameter of 6 mm is used as the transferring tube. The hydroxyapatite suspension which contains the pore-forming agent ammonium carbonate is injected into the small-diameter catheter with a 100 microns inner diameter at a transferring rate of 15 ml/min. The hydroxyapatite suspension is injected into the high temperature area of the central plasma flame through the small-diameter catheter in the form of linear jet flow. The plasma flame is generated by the direct current plasma spraying device. The spraying power is 50 KW and the spraying distance is 14 cm. The hydroxyapatite suspension makes the heat exchange with the high temperature plasma flame. After the suspension is subjected to fragmentation and refining of droplets, solvent evaporation, decomposition and gasification of pore-forming agent, and melting of spraying feedstock materials, the porous hydroxyapatite coatings are directly deposited on the biomedical titanium alloy substrate surfaces. The SEM micrograph of the coating is shown in FIG. 5.

EXAMPLE 4

The Preparation of the Porous Hydroxyapatite Coating from the Present Invention

Figure 6:
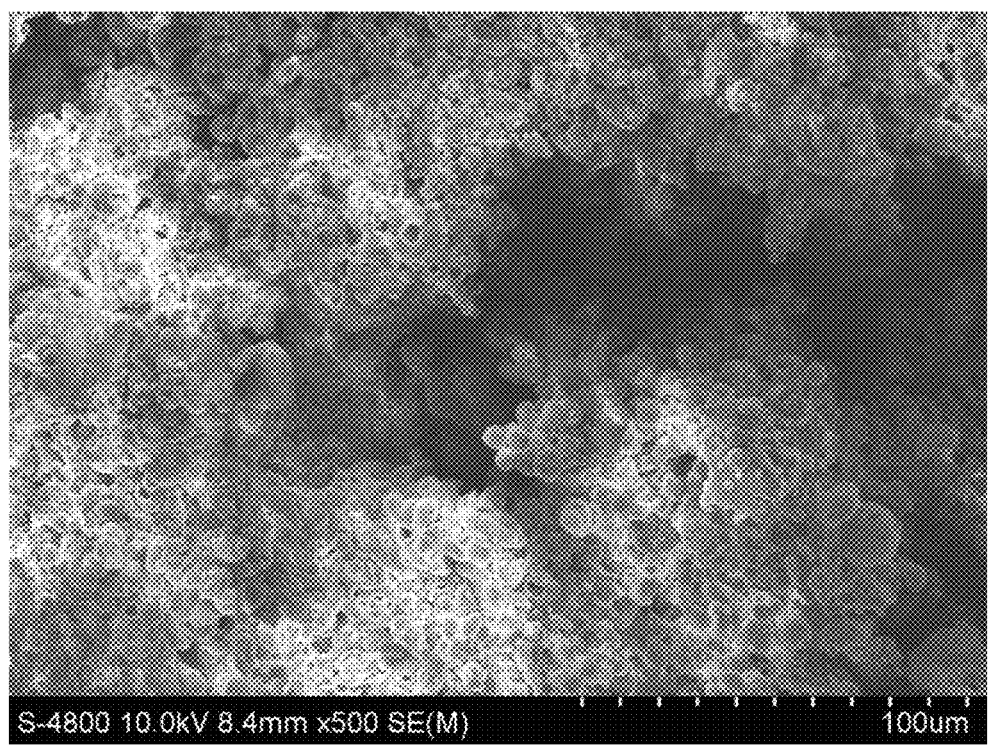
FIG. 6: SEM micrograph of hydroxyapatite coating prepared by the suspension plasma spraying process (with the addition of ammonium bicarbonate as the pore-forming agent).

The 1.8 mol/L diammonium phosphate solution is added into a stirred 1.5 mol/L calcium nitrate solution on the basis of a Ca/P molar ratio of $Ca_{10}(PO_4)_6(OH)_2$. The pH value of the solution mixture is adjusted to 9 with 30 wt % ammonia solution and the reaction was kept at 80° C. for 15 min, followed by aging for 48 h. After the above steps, hydroxyapatite suspension with a 22% solid content is obtained. The pore-forming agent ammonium bicarbonate is added into the hydroxyapatite suspension. If the solid content of suspension is referred to as 100%, the amount of the added ammonium bicarbonate is 40%. The electronic peristaltic pump is used as the transferring power. The pressure tube with a diameter of 8 mm is used as the transferring tube. The hydroxyapatite suspension with the addition of the pore-forming agent ammonium bicarbonate is transferred into the small-angle atomization nozzle with 20 degree spray angle at a transferring rate of 90 ml/min. The atomization nozzle uses the compressed air as the atomization gas and the atomization pressure is 0.1 MPa. After the atomization, the hydroxyapatite suspension is directly injected into the high temperature area of the plasma flame through radial direction. The plasma flame is generated by the direct current plasma spraying device. The spraying power is 35 KW and the spraying distance is 8 cm. The hydroxyapatite suspension makes the heat exchange with the high temperature plasma flame. After the suspension is subjected to fragmentation and refining of droplets, solvent evaporation, decomposition and gasification of pore-forming agent, and melting of spraying feedstock materials, the porous hydroxyapatite coatings are directly deposited on the biomedical co-based alloy substrate surfaces. The SEM micrograph of the coating is shown in FIG. 6.

EXAMPLE 5

The Preparation of the Porous Hydroxyapatite Coating from the Present Invention

Figure 7:
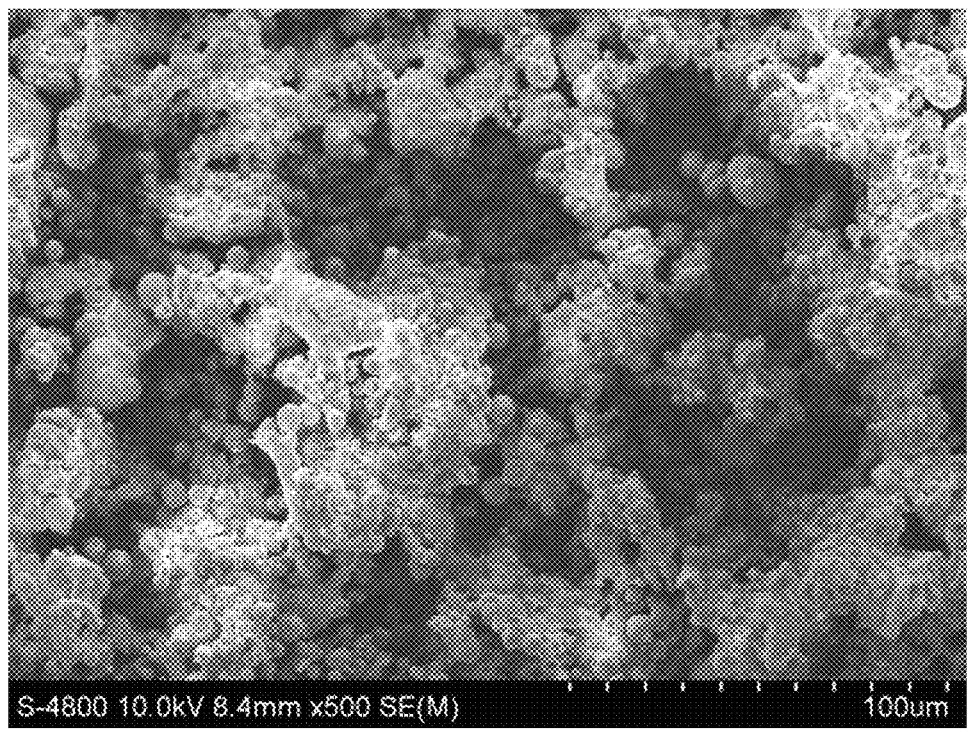
FIG. 7: SEM micrograph of hydroxyapatite coating prepared by the suspension plasma spraying process (with the addition of hydrogen peroxide as the pore-forming agent).

The 3 mol/L diammonium phosphate solution is added into a stirred 2.5 mol/L calcium nitrate solution on the basis of a Ca/P molar ratio of $Ca_{10}(PO_4)_6(OH)_2$. The pH value of the solution mixture is adjusted to 11 with 20 wt % ammonia solution and the reaction was kept at 90° C. for 10 min, followed by aging for 24 h. After the above steps, hydroxyapatite suspension with a 35% solid content is obtained. The pore-forming agent hydrogen peroxide is added into the hydroxyapatite suspension. If the volume of suspension is referred to as 100%, the volume of the added hydrogen peroxide is 25%. The compressed air with 0.3 MPa pressure is used as the transferring power. The pressure tube with a diameter of 6 mm is used as the transferring tube. The hydroxyapatite suspension with the addition of the pore-forming agent hydrogen peroxide is transferred into the small-diameter catheter with the inner diameter of 80 microns. The spraying liquid is injected into the high temperature area of the central plasma flame through small-diameter catheter in the form of linear jet flow. The plasma flame is generated by the direct current plasma spraying device. The spraying power is 40 KW and the spraying distance is 10 cm. The hydroxyapatite suspension makes the heat exchange with the high temperature plasma flame. After the suspension is subjected to fragmentation and refining of droplets, solvent evaporation, decomposition and gasification of pore-forming agent, and melting of spraying feedstock materials, the porous hydroxyapatite coatings are directly deposited on the biomedical zirconia ceramic substrate surfaces. The SEM micrograph of the coating is shown in FIG. 7.

Test Example 1

Figure 2:
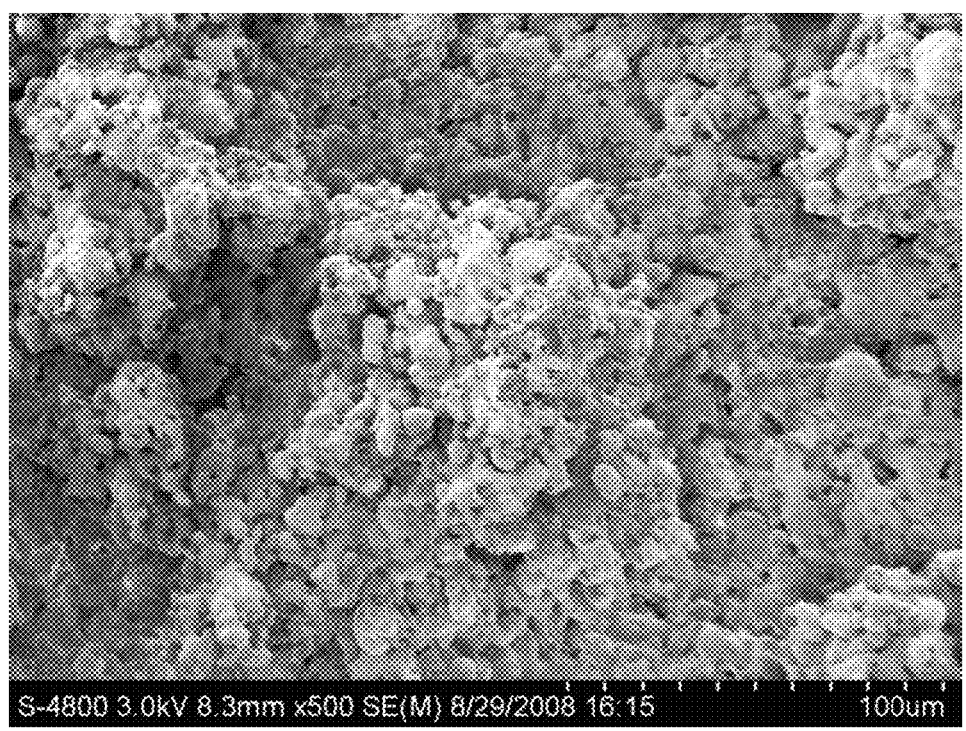
FIG. 2: SEM micrograph of hydroxyapatite coating prepared by the suspension plasma spraying process (without the addition of pore-forming agent).

The Bioactivity Test of the Porous Hydroxyapatite Coatings Synthesized from the Present Invention 1. The hydroxyapatite coatings prepared by the existing technique The same conditions as the Example 1 are selected, except that the hydroxyapatite suspension without any addition of the pore-forming agent ethanol is selected. The SEM micrograph of the coating is shown in FIG. 2.

2. In the ultra-clean workbench, the air plasma sprayed hydroxyapatite coatings, suspension plasma sprayed hydroxyapatite coatings (without the addition of the pore-forming agent) and suspension plasma sprayed hydroxyapatite coatings (with the addition of the deionzed water as the pore-forming agent, see details in the Example 2) are put into 24-well culture plate with three parallel for each kind of sample. At the same time, the corresponding blank holes are left as the control. The osteoblastic MG-63 cells which almost completely covered the culture disk are digested by the 0.25% trypsin. After the fresh DMEM culture medium which contains 10% fetal bovine serum is added into the osteoblastic cells, the cell suspension with a cell concentration of $1 \times 10^4$ $ml^{-1}$ is obtained. Then, the cell suspension is added into these coating sample and blank control wells with the amount of 1 ml for each well. The culture plates are put into $CO_2$ incubator with a constant temperature for 2 and 4 days. The culture medium was renewed every two days. Then, the effects of different kinds of coatings on the osteoblastic cell's proliferation and growth are analyzed by MTT method. The detailed method is as follows: the 5 mg/ml MTT solution is prepared; the MTT solution is added into the coating sample and blank control wells which have been cultured for 2 and 4 days. Then, the culture plates are put into the $CO_2$ incubator with a constant temperature for 4 h. After 4 h, the liquids of these wells are discarded. After the dimethyl sulfoxide (DMSO) is added into these wells with the amount of 1 ml/well, these culture plates are put on the vibrator for 5 min. Then the liquid of these wells are transferred into the 96-well plate. The optical density (OD) values of these wells are tested by the Enzyme-linked immunosorbent assay at 490 nm. The higher the OD values are, the higher the osteoblastic cell proliferation, growth and bioactivity of the samples are. The detailed test results are shown in Table 1.

TABLE 1

| Sample type | OD values | |
|---|---|---|
| | 2 days | 4 days |
| Air plasma sprayed hydroxyapatite coatings | 0.651 ± 0.0148 | 1.102 ± 0.0350 |
| Suspension plasma sprayed hydroxyapatite coatings (without the pore-forming agent) | 0.706 ± 0.0172 | 0.976 ± 0.0548 |
| Suspension plasma sprayed hydroxyapatite coatings (with the pore-forming agent) | 0.767 ± 0.0251 | 1.268 ± 0.233 |
| Blank control | 0.625 ± 0.00902 | 0.993 ± 0.0334 |

The results of the above table show that the OD value of the suspension plasma sprayed hydroxyapatite coatings with the addition of the pore-forming agent is higher than that of the blank control. It indicates that the coatings are beneficial to the proliferation and growth of the cells, in addition to the lack of cytotoxicity. At the same time, the OD value of the suspension plasma sprayed hydroxyapatite coatings with the addition of the pore-forming agent is higher than those of the air plasma sprayed hydroxyapatite coatings and suspension plasma sprayed hydroxyapatite coatings without the addition of the pore-forming agent. It shows that the bioactivity, osteoblastic cell proliferation and growth of the porous hydroxyapatite coatings made by suspension plasma spraying with the addition of the pore-forming agent are better than those of the air plasma sprayed hydroxyapatite coatings and suspension plasma sprayed hydroxyapatite coating without the addition of the pore-forming agent.

The invention claimed is:

1. A method for preparing a porous hydroxyapatite coating through suspension plasma spraying, said method comprising:
    adding a pore-forming agent to a hydroxyapatite suspension having a solids content of 16%-45% to form a liquid feedstock, wherein the pore-forming agent comprises at least one member selected from the group consisting of ammonium carbonate and ammonium bicarbonate and is added to the hydroxyapatite suspension in an amount of 5%-65% based on a solids content of the suspension being referred to as 100%, and optionally further comprises at least one additional pore-forming agent selected from the group consisting of ethanol, hydrogen peroxide and deionized water;
    injecting into a central plasma flame the liquid feedstock so as to produce a plasma spray; and
    depositing onto a substrate surface of a biomedical material the porous hydroxyapatite coating from the plasma spray.

2. The method of claim 1, wherein the pore-forming agent is one of ammonium carbonate or ammonium bicarbonate and there is no additional pore-forming agent.

3. The method of claim 1, wherein the at least one additional pore-forming agent is ethanol or hydrogen peroxide and is added to the hydroxyapatite suspension in an amount of 10%-80% based on a solids content of the suspension being referred to as 100%.

4. The method of claim 1, wherein the at least one additional pore-forming agent is deionized water and is added into the suspension so as to reduce the solids content of the suspension to 5%-15%.

5. The method of claim 1, wherein the hydroxyapatite suspension is prepared by the following steps:
   (a) adding 1.2-3.6 mol/L diammonium phosphate solution to a stirred 1-3 mol/L calcium nitrate solution according to a Ca/P molar ratio of $Ca_{10}(PO_4)_6(OH)_2$ to provide a mixture;
   (b) adjusting a pH value of the mixture from step (a) to 9-12 with 30 wt % ammonia solution;
   (c) maintaining a temperature of the mixture from step (b) at 30-90° C. for 5-15 min; and
   (d) aging the mixture of step (c) for 24-48 hours to provide the hydroxyapatite suspension.

6. The method of claim 1, wherein the liquid feedstock for plasma spraying is directly injected into the central plasma flame along a radial direction, by using either a small-angle atomization nozzle or a small-diameter catheter.

7. The method of claim 5, wherein:
   (i) the pore-forming agent is one of ammonium carbonate or ammonium bicarbonate and there is no additional pore-forming agent;
   (ii) the liquid feedstock is transferred into an injection system for injecting the suspension into the central plasma flame using: (a) an electronic peristaltic pump with a transferring rate of 10-100 ml/min and a pressure tube with an inner diameter of 5-10 mm; or (b) compressed air with a pressure of 0.15-0.6 MPa;
   (iii) the liquid feedstock is injected along a radial direction into the central plasma flame through: (a) a small-angle nozzle to atomize the spraying liquid; or (b) a small-diameter catheter in a mode of linear jet flow, and undergoes heat exchange with the plasma flame, breakup and refinement of suspension droplets, solvent evaporation, decomposition and gasification of the pore-forming agent and melting of feedstock materials, such that the porous hydroxyapatite coating is directly deposited onto substrate surfaces of the biomedical material.

8. The method of claim 7, wherein the transferring rate of the electronic peristaltic pump is 15-90 ml/min, and the inner diameter of the pressure tube is 5-10 mm; or the pressure of the compressed air is 0.2-0.5 MPa.

9. The method of claim 7, wherein a spraying angle of the small-angle nozzle is 10-25 degrees.

10. The method of claim 7, wherein the atomization nozzle uses the compressed air as an atomizing gas, and the pressure is 0.1-0.5 MPa.

11. The method of claim 7, wherein an inner diameter of the small-diameter catheter is 60-280 microns.

12. The method of claim 7, wherein a spraying power is 20-70 KW.

13. The method of claim 7, wherein a spraying distance between the biomedical material and the nozzle is 8-18 cm.

14. The method of claim 7, wherein the biomedical material is biomedical titanium, biomedical titanium alloys, biomedical stainless steels, biomedical cobalt-based alloys, other biomedical metal materials, biomedical ceramic materials, or biomedical composite materials which contain a metal or a ceramic.

15. A method for preparing a porous hydroxyapatite coating through suspension plasma spraying, said method comprising:
   adding a pore-forming agent to a hydroxyapatite suspension having a solids content of 16%-45% to form a liquid feedstock, wherein the pore-forming agent comprises at least one member selected from the group consisting of ammonium carbonate and ammonium bicarbonate, which is added to the hydroxyapatite suspension in an amount of 5%-65% based on a solids content of the suspension being referred to as 100%, and (b) at least one additional pore-forming agent selected from the group consisting of ethanol, hydrogen peroxide and deionized water;
   injecting into a central plasma flame the liquid feedstock so as to produce a plasma spray; and
   depositing onto a substrate of a biomedical material the porous hydroxyapatite coating from the plasma spray.

* * * * *